(12) United States Patent
DaSilva et al.

(10) Patent No.: US 10,857,856 B2
(45) Date of Patent: Dec. 8, 2020

(54) VEHICLE MOUNTED SCENT DISPENSER

(71) Applicants: Debora DaSilva, Sacramento, CA (US); Stefan Tramel, Sacramento, CA (US)

(72) Inventors: Debora DaSilva, Sacramento, CA (US); Stefan Tramel, Sacramento, CA (US)

( * ) Notice: Subject to any disclaimer, the term of this patent is extended or adjusted under 35 U.S.C. 154(b) by 353 days.

(21) Appl. No.: 15/919,929

(22) Filed: Mar. 13, 2018

(65) Prior Publication Data
US 2019/0283545 A1    Sep. 19, 2019

(51) Int. Cl.
*A61L 9/00* (2006.01)
*B60H 3/00* (2006.01)
*A61L 9/14* (2006.01)

(52) U.S. Cl.
CPC ......... *B60H 3/0014* (2013.01); *B60H 3/0035* (2013.01); *A61L 9/14* (2013.01); *B60H 2003/0042* (2013.01)

(58) Field of Classification Search
CPC ..... A61L 9/14; A61L 2/20; A61L 2/00; A61L 2/0094; B60H 3/0035; B60H 3/0014; B60N 2/5657; B60N 2/5671
USPC ..................................................... 422/5, 305
See application file for complete search history.

(56) References Cited

U.S. PATENT DOCUMENTS

| | | |
|---|---|---|
| 5,102,189 A | 4/1992 | Saito et al. |
| 5,833,929 A | 11/1998 | Watson et al. |
| 6,181,996 B1 | 1/2001 | Chou et al. |
| 8,454,094 B1 | 6/2013 | Boulware, Sr. |
| 8,510,984 B2 | 8/2013 | Burgeson |
| D696,762 S | 12/2013 | Lin |
| 2008/0060119 A1 | 3/2008 | Pinizzotto |

FOREIGN PATENT DOCUMENTS

WO   WO 2009/024227   *  2/2009   ............... B60N 2/56
WO   WO2009024227       2/2009

OTHER PUBLICATIONS

European Patent Office English Translation of the Description and The Claims Sections of WO 2009/024227.*

* cited by examiner

*Primary Examiner* — Monzer R Chorbaji

(57) ABSTRACT

A vehicle mounted scent dispenser for releasing a scent when a driver sits in a driver's seat includes a vehicle that has an interior. A driver's seat is mounted on the interior. A dispensing unit is also mounted in the interior of the vehicle. The dispensing unit dispenses scented air into the interior of the vehicle when the dispensing unit is actuated. A switch is in communication with the dispensing unit and the driver's seat. The switch turns on the dispensing unit when a person sits on the driver's seat.

4 Claims, 6 Drawing Sheets

VEHICLE MOUNTED SCENT DISPENSER

(b) CROSS-REFERENCE TO RELATED APPLICATIONS

Not Applicable

(c) STATEMENT REGARDING FEDERALLY SPONSORED RESEARCH OR DEVELOPMENT

Not Applicable

(d) THE NAMES OF THE PARTIES TO A JOINT RESEARCH AGREEMENT

Not Applicable

Figure 1:
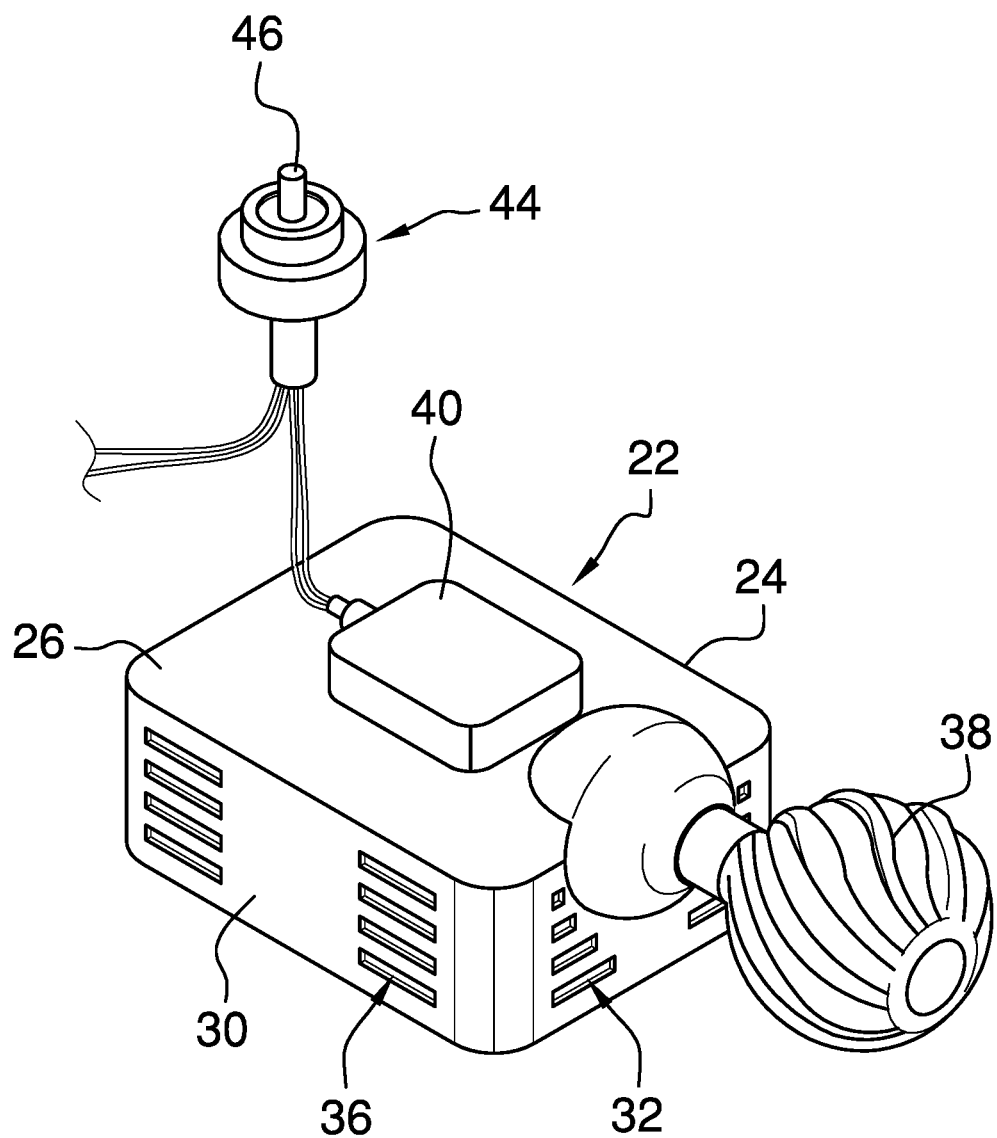

(e) INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

(f) STATEMENT REGARDING PRIOR DISCLOSURES BY THE INVENTOR OR JOINT INVENTOR

Not Applicable

(g) BACKGROUND OF THE INVENTION (1) Field of the Invention
(2) Description of Related Art Including Information Disclosed Under 37 CFR 1.97 and 1.98.

The disclosure and prior art relates to switch actuated scent releasing systems and more particularly pertains to a new switch actuated scent releasing system for releasing a scent when a driver sits in a driver's seat.

(h) BRIEF SUMMARY OF THE INVENTION

An embodiment of the disclosure meets the needs presented above by generally comprising a vehicle that has an interior. A driver's seat is mounted on the interior. A dispensing unit is also mounted in the interior of the vehicle. The dispensing unit dispenses scented air into the interior of the vehicle when the dispensing unit is actuated. A switch is in communication with the dispensing unit and the driver's seat. The switch turns on the dispensing unit when a person sits on the driver's seat.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

(i) BRIEF DESCRIPTION OF SEVERAL VIEWS OF THE DRAWING(S)

Figure 2:
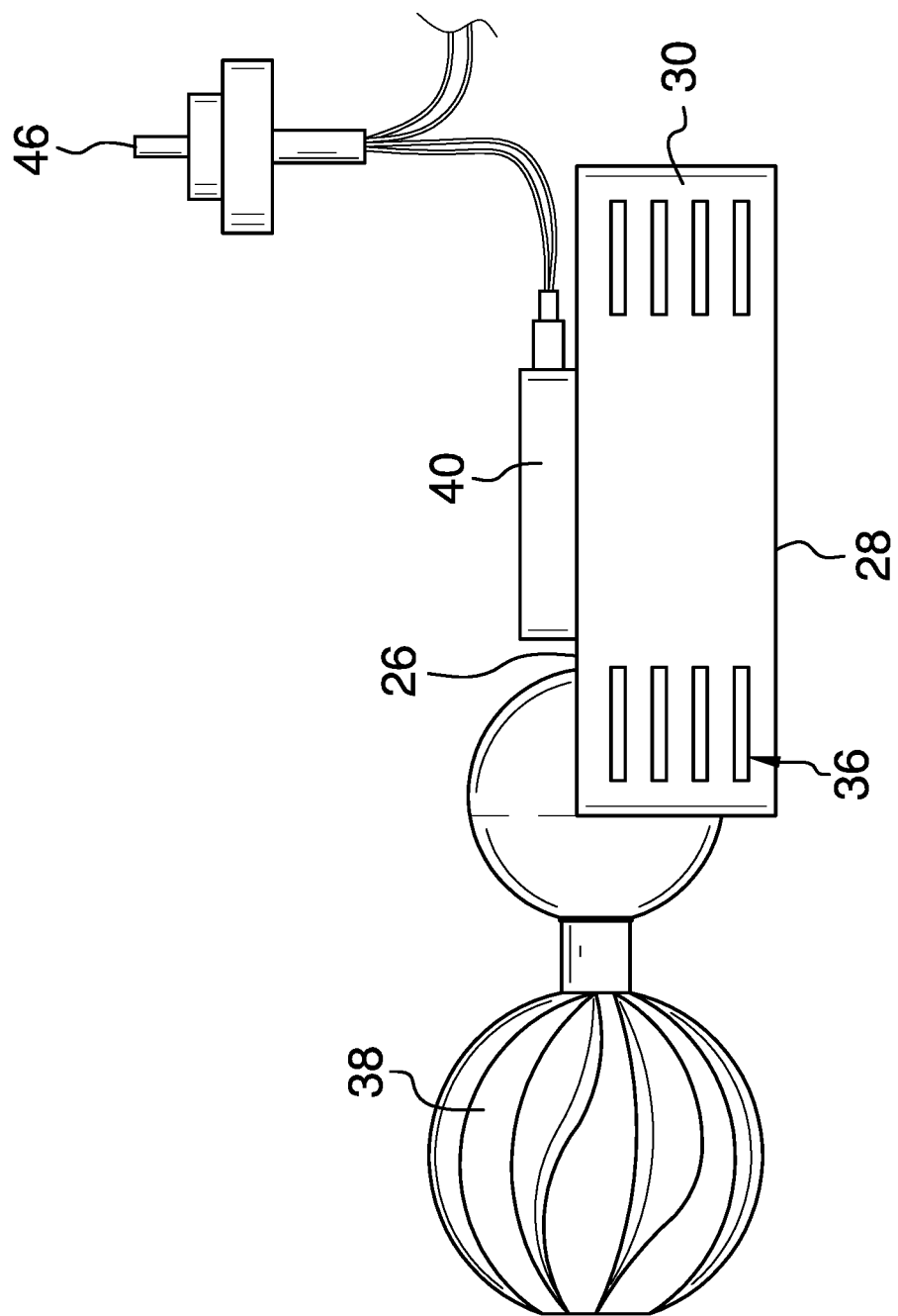
Figure 3:
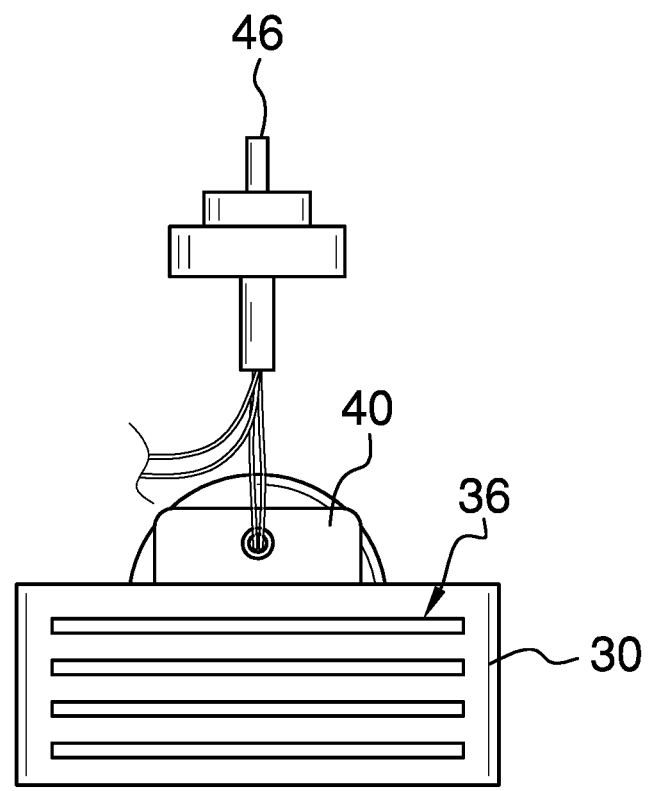
Figure 4:
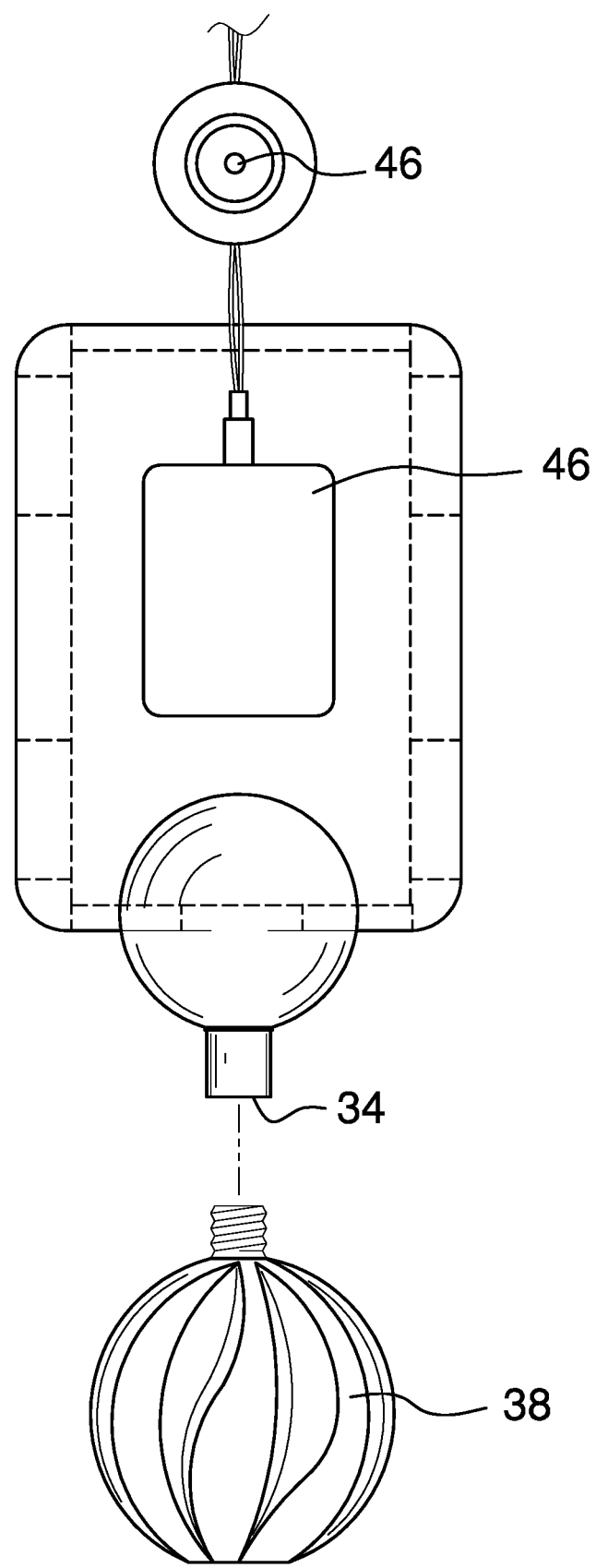
Figure 5:
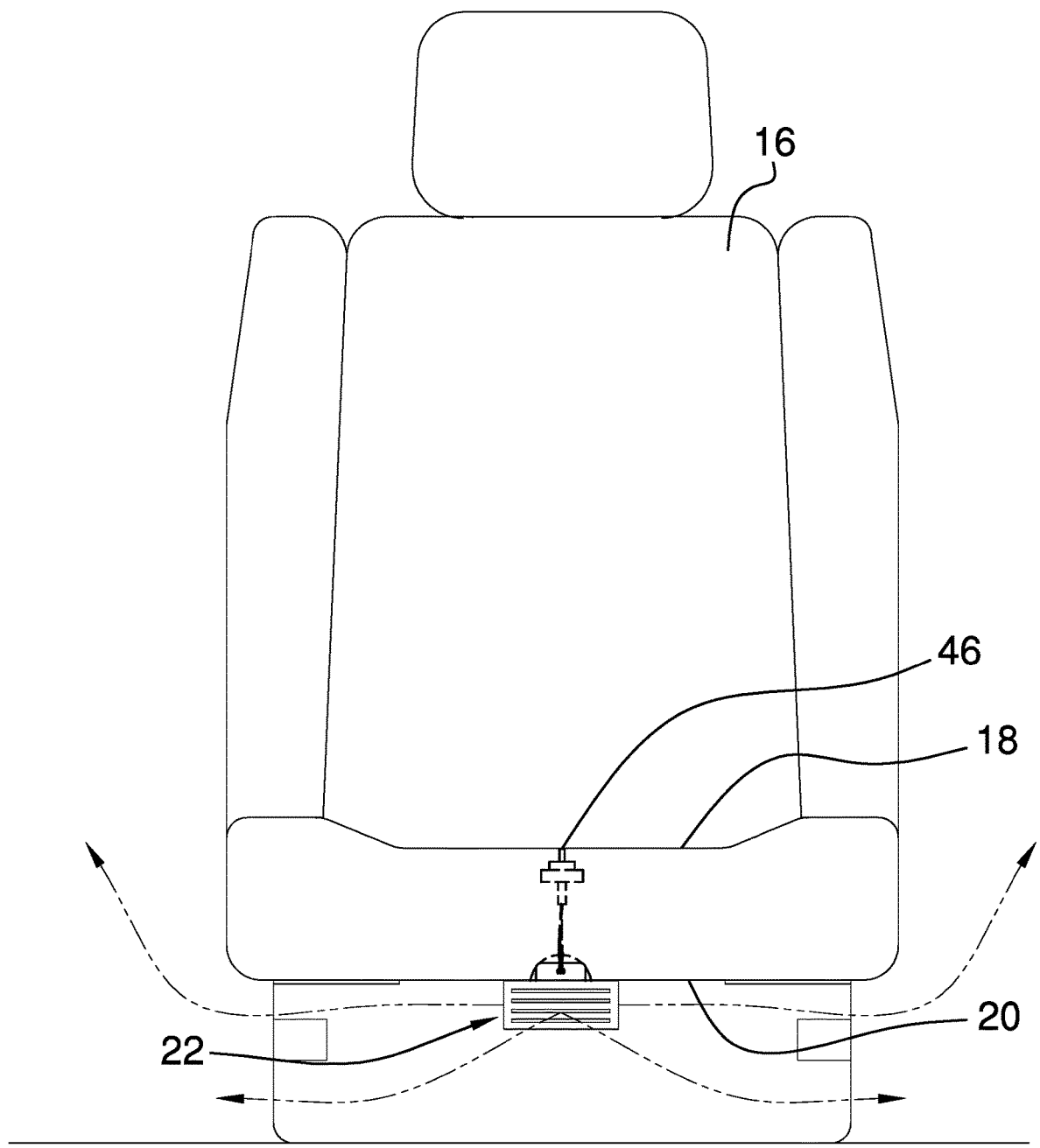
Figure 6:
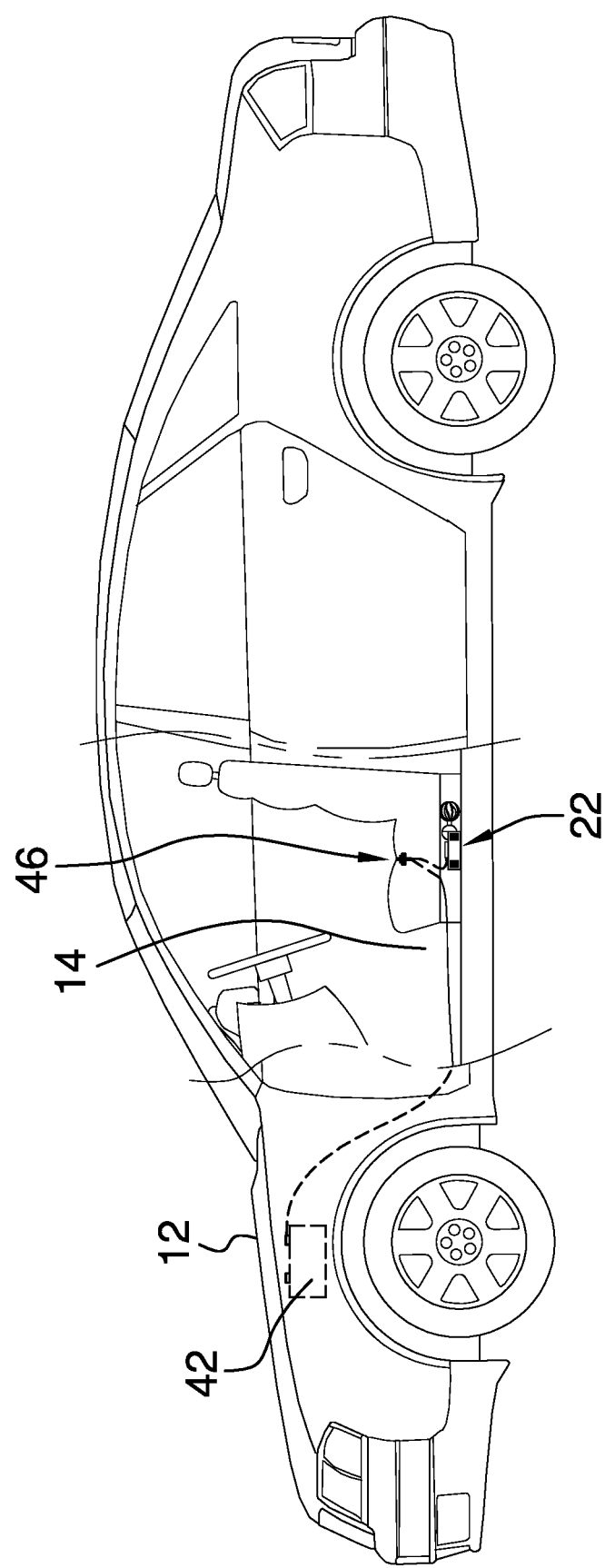

The disclosure will be better understood and objects other than those set forth above will become apparent when consideration is given to the following detailed description thereof. Such description makes reference to the annexed drawings wherein:

FIG. 1 is a top side view of a vehicle mounted scent dispenser according to an embodiment of the disclosure.
FIG. 2 is a side view of an embodiment of the disclosure.
FIG. 3 is a top view of an embodiment of the disclosure.
FIG. 4 is a back view of an embodiment of the disclosure.
FIG. 5 is a front view of an embodiment of the disclosure.
FIG. 6 is a side view of an embodiment of the disclosure.

(j) DETAILED DESCRIPTION OF THE INVENTION

With reference now to the drawings, and in particular to FIGS. 1 through 6 thereof, a new switch actuated scent releasing system embodying the principles and concepts of an embodiment of the disclosure and generally designated by the reference numeral 10 will be described.

As best illustrated in FIGS. 1 through 6, the vehicle mounted scent dispenser 10 generally comprises a vehicle 12 that has an interior 14. A driver's seat 16 is mounted on the interior 14 and has a top side 18 and a bottom side 20. A dispensing unit 22 is mounted in the interior 14 of the vehicle 12 and dispenses scented air into the interior 14 of the vehicle 12 when the dispensing unit 22 is actuated.

The dispensing unit 22 comprises a housing 24 that has a top wall 26, a bottom wall 28 and a perimeter wall 30 that is attached to and extends between the top wall 26 and the bottom wall 28. The perimeter wall 30 has at least one and may includes a plurality of intake apertures 32 that extend therein to intake air from outside of the housing 24. The housing 24 has an inlet aperture 34 that extends therein. The housing 24 also has at least one and may have a plurality of outlet apertures 36 that extend therein. The housing 24 is positioned under the bottom side 20 of the driver's seat 16.

A scent container 38 is included and contains a fluid scent therein. The scent container 38 is fluidly coupled to the inlet aperture 34. A pump 40 is in fluid communication with the intake apertures 32, the inlet aperture 34 and the outlet apertures 36. The pump 40 mixes the fluid scent with air from the intake apertures 34 to define an aerosolized scent that is dispensed from the outlet apertures 36. A power supply 42 is electrically coupled to the dispensing unit 22 and may comprise an electrical power system of the vehicle 12.

A switch 44 is in communication with the dispensing unit 22 and the driver's seat 16. The switch 44 turns on the dispensing unit 22 when a person sits on the driver's seat 16. The switch 44 comprises a pressure sensor 46 that is mounted on the driver's seat 16 wherein the pressure sensor 46 detects a threshold weight. The switch 44 turns on the dispensing unit 22 to dispense a burst of the scented air when the threshold weight is detected. The threshold weight is greater than 50.0 lbs and the burst may last between less than 0.1 seconds and up to 5.0 seconds.

In use, the dispensing unit 22 is positioned under the bottom side 20 of the driver's seat 16. The switch 44 is in communication with the driver's seat 16 such that when the person sits in the driver's seat 16 and the threshold weight is met the switch 44 actuates the dispensing unit 22. When actuated the pump 40 of the dispensing unit 22 takes in and mixes the fluid scent with the air from outside the housing to define the aerosolized scent that is then dispersed from each of the outlet apertures 36.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. A scent dispensing system configured to release scented air, said system comprising:
   a vehicle having an interior;
   a driver's seat being mounted on said interior, said driver's seat having a top side and a bottom side;
   a dispensing unit being mounted in said interior of said vehicle, said dispensing unit dispensing scented air into said interior of said vehicle when said dispensing unit is actuated; and
   a switch being in communication with said dispensing unit and said driver's seat, said switch turning on said dispensing unit when a person sits on said driver's seat, said switch comprising a pressure sensor being mounted on said driver's seat wherein said pressure sensor detects a threshold weight, said switch turning on said dispensing unit to dispense a burst of the scented air when said threshold weight is detected.

2. The scent dispensing system according to claim 1, wherein said pump unit comprises:
   a housing having a top wall, a bottom wall and a perimeter wall being attached to and extending between said top wall and said bottom wall, said perimeter wall having a plurality of intake apertures extending therein to intake air from outside of said housing, said housing having an inlet aperture extending therein, said housing having a plurality of outlet apertures extending therein, said housing being positioned under said bottom side of said driver's seat;
   a scent container containing a fluid scent, said scent container being fluidly coupled to said inlet aperture;
   a pump being in fluid communication with said intake apertures, said inlet aperture and said outlet apertures, said pump mixing said fluid scent with air from said intake apertures to define an aerosolized scent dispensed from said outlet apertures; and
   a power supply being electrically coupled to said dispensing unit, said power supply comprising an electrical power system of a vehicle.

3. The scent dispensing system according to claim 1, wherein said threshold weight is greater than 50.0 lbs.

4. A scent dispensing system configured to release scented air, said system comprising:
   a vehicle having an interior;
   a driver's seat being mounted on said interior, said driver's seat having a top side and a bottom side;
   a dispensing unit being mounted in said interior of said vehicle, said dispensing unit dispensing scented air into said interior of said vehicle when said dispensing unit is actuated, said dispensing unit comprising:
      a housing having a top wall, a bottom wall and a perimeter wall being attached to and extending between said top wall and said bottom wall, said perimeter wall having a plurality of intake apertures extending therein to intake air from outside of said housing, said housing having an inlet aperture extending therein, said housing having a plurality of outlet apertures extending therein, said housing being positioned under said bottom side of said driver's seat;
      a scent container containing a fluid scent, said scent container being fluidly coupled to said inlet aperture;
      a pump being in fluid communication with said intake apertures, said inlet aperture and said outlet apertures, said pump mixing said fluid scent with air from said intake apertures to define an aerosolized scent dispensed from said outlet apertures;
      a power supply being electrically coupled to said dispensing unit, said power supply comprising an electrical power system of a vehicle;
   a switch being in communication with said dispensing unit and said driver's seat, said switch turning on said dispensing unit when a person sits on said driver's seat, said switch comprising a pressure sensor being mounted on said driver's seat wherein said pressure sensor detects a threshold weight, said switch turning on said dispensing unit to dispense a burst of the scented air when said threshold weight is detected, said threshold weight being greater than 50.0 lbs.

* * * * *